(12) United States Patent　　(10) Patent No.: US 9,238,789 B2
Niazi　　(45) Date of Patent: Jan. 19, 2016

(54) BAFFLED SINGLE USE BIOREACTOR

(75) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 0 days.

(21) Appl. No.: 13/555,149

(22) Filed: Jul. 21, 2012

(65) Prior Publication Data

US 2014/0024105 A1　　Jan. 23, 2014

(51) Int. Cl.
*A01N 1/00*　　(2006.01)
*C12M 1/00*　　(2006.01)
*C12M 3/06*　　(2006.01)

(52) U.S. Cl.
CPC .............. *C12M 27/20* (2013.01); *C12M 23/26* (2013.01); *C12M 23/34* (2013.01); *C12M 27/16* (2013.01); *C12M 29/06* (2013.01); *C12M 29/20* (2013.01)

(58) Field of Classification Search
CPC ...... C12M 23/26; C12M 23/34; C12M 27/20; C12M 29/06; C12M 29/20
USPC .......... 435/283.1, 284.1, 286.1, 286.2, 286.5, 435/286.6, 287.1, 288.1, 288.2, 288.3, 435/288.4, 288.5, 289.1, 290.2
See application file for complete search history.

(56) References Cited

U.S. PATENT DOCUMENTS

| | | | |
|---|---|---|---|
| 6,190,913 B1 * | 2/2001 | Singh | 435/394 |
| 2004/0048364 A1 * | 3/2004 | Trosch | 435/292.1 |
| 2004/0159616 A1 * | 8/2004 | Cohee et al. | 210/767 |
| 2005/0013870 A1 * | 1/2005 | Freyman et al. | 435/325 |
| 2005/0186669 A1 * | 8/2005 | Ho et al. | 435/287.1 |
| 2008/0274541 A1 * | 11/2008 | Selker et al. | 435/289.1 |
| 2010/0015696 A1 | 1/2010 | Claes et al. | |
| 2011/0124087 A1 * | 5/2011 | Meiser et al. | 435/292.1 |
| 2011/0198286 A1 | 8/2011 | Niazi | |
| 2011/0217690 A1 | 9/2011 | Niazi | |

OTHER PUBLICATIONS

International Search Report and Written Opinion of PCT/US2013/051119, dated Nov. 29, 2013.

* cited by examiner

*Primary Examiner* — Nathan Bowers
*Assistant Examiner* — Timothy Barlow
(74) *Attorney, Agent, or Firm* — Therapeutic Proteins International, LLC; Cheryl Liljestrand; Sarfaraz K. Niazi

(57) ABSTRACT

A flexible disposable bioreactor having three, stagger-baffled compartments wherein the middle compartment houses a sparging rod is described to provide the highest degree of sparging and mixing to produce biological products.

10 Claims, 2 Drawing Sheets

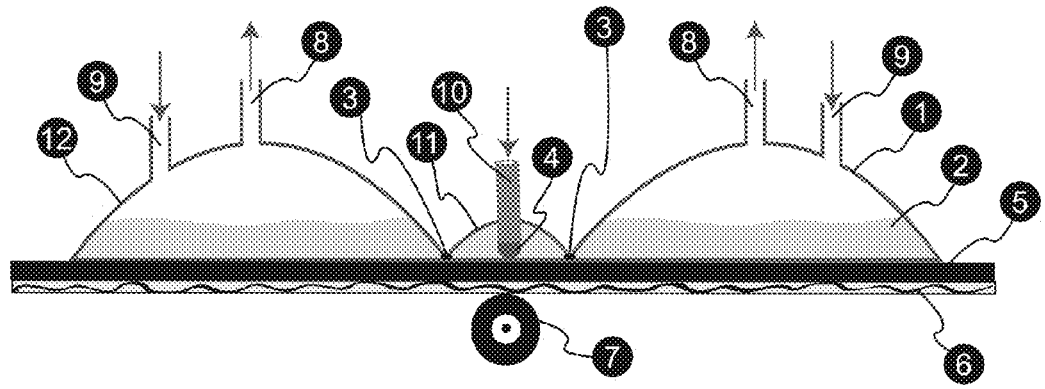
Figure 1A
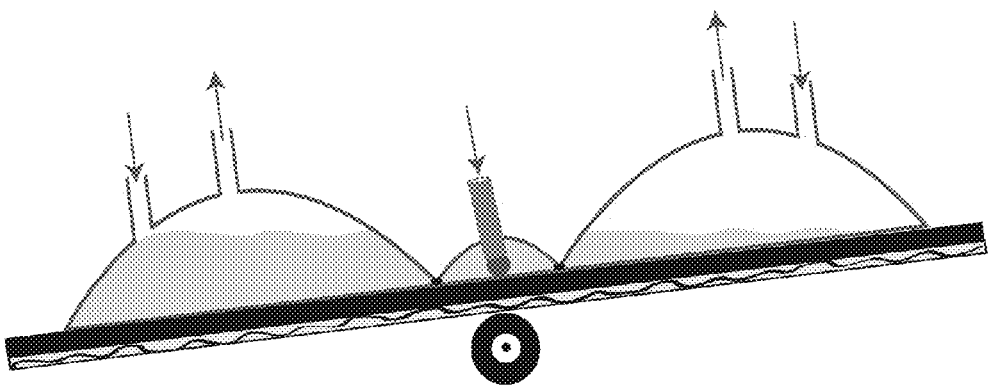
Figure 1B
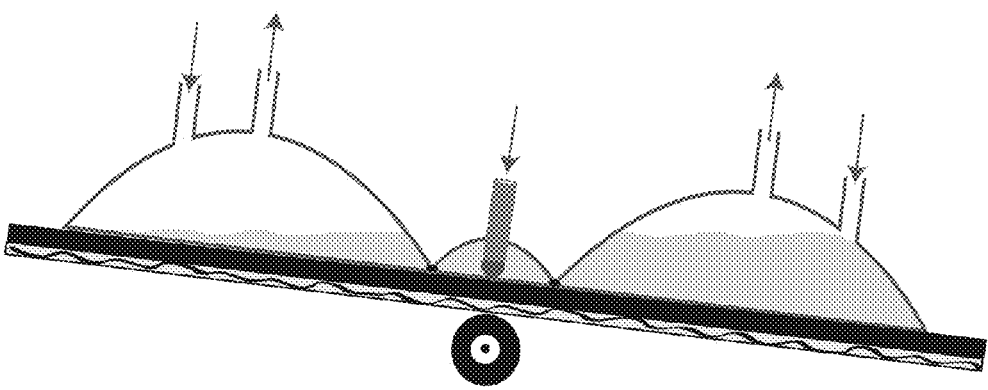
Figure 1C
Figure 1

BAFFLED SINGLE USE BIOREACTOR

TECHNICAL FIELD

The present invention relates generally to single-use flexible bioreactor capable of growing bacteria, mammalian cells, plant cells and viruses.

BACKGROUND OF THE INVENTION

Traditional bioreactors trace their design back to the vessels used in the fermentation industry for over 7,000 years. Most pharmaceutical solutions and suspensions manufactured on an industrial scale require highly controlled, thorough mixing to achieve a satisfactory yield and ensure a uniform distribution of ingredients in the final product. Agitator tanks are frequently used to complete the mixing process, but a better degree of mixing is normally achieved by using a mechanical stirrer or impeller (e.g., a set of mixing blades attached to a metal rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

In an effort to overcome these problems, the recent trend in the biotechnology industry is to use disposable plastic bags for a number of bioprocessing steps. Pre-sterilized disposable plastic bags eliminate the need for cleaning, sterilization and validation of the containers after each bioprocessing batch. Their use thus results in substantial saving in the cost of manufacturing of biopharmaceuticals.

Typically, one of the bioprocessing steps used in such manufacturing is growing cell culture(s) in the container, sometimes called a "bioreactor." A traditional bioreactor is a sterile vessel made out of stainless steel or glass with highly controlled environmental parameters including temperature, pH, oxygen concentration, carbon dioxide concentration, which are monitored by permanent sensors built into the rigid vessel. During the cell growth process, the fluid in the bioreactor must also be agitated in order to maintain uniform distribution of temperature, gases and nutrients. As noted above, an impeller typically provides agitation with the blades housed on the shaft connected to an external motor and introduced inside the bioreactor through the dynamic seal in an effort to maintain sterility.

For normal cell growth certain concentration of dissolved oxygen must be maintained. Also, controlled introduction of other gases like carbon dioxide and nitrogen are normally necessary during bioreactor runs. The most efficient way of introducing gases in to bioreactor fluid is sparging, which involves forming small bubbles in the fluid. Such bubbles have large surface to volume ratio and thus can be dissolved more quickly than large size bubbles and thus provide a large kLA value (transport across fluid air interface).

Traditionally, porous solid materials (like titanium) associated with the rigid bioreactor provide sparging. Alternatively, metal sparging rings with small pre-drilled holes are permanently affixed in some rigid bioreactors. In both cases, the bioreactors are not readily disposable and thus must be cleaned and sterilized before reuse for bioprocessing.

In traditional rigid vessel bioreactor, the impeller, sparger, gas, temperature and pH sensors are reusable components that must be cleaned and sterilized after each batch. In the case of disposable bag bioreactors, it is desirable that all the fluid touching components are only used once. This presents the challenging task of providing inexpensive fluid-touching components that can be discarded along with the bag after use.

Another challenge is positioning the components of the bioreactor on the flexible bag. Unlike a rigid vessel, a bioreactor plastic bag (which is basically thin film) has no shape or structural rigidity. Traditionally, bioreactor components like impeller shafts, spargers, and sensors are housed on the rigid walls of the vessel by means of threads, bolts or clamps. Obviously, this method of component attachment does not work for plastic bags. To overcome this, many manufacturers offer such solutions as levitating mixing devices, rocking and shaking of bags or compressing the bag externally to produce a wave motion inside the bag. While all of these methods provide some solutions to the problem, many problems in the mixing and aeration remain.

Thus, a need is identified for an improved manner of providing a mixing bag or flexible vessel with an integrated sparger and sensor(s). The improvement provided by the invention would be easy to implement using existing manufacturing techniques and without significant additional expense. Overall, a substantial gain in efficiency and ease of use would be realized as a result of the improvement, and would greatly expand the potential applications for which advanced mixing systems may be used, including bioprocessing.

SUMMARY OF THE INVENTION

A disposable bioprocessing apparatus intended for receiving a fluid in need of agitation and sparging using a gas is provided. The apparatus according to one aspect of the disclosure comprises a bag having an upper and a lower flexible wall forming an interior compartment capable of receiving and holding the fluid; the bag is divided into three compartments using two rows of proportionally spaced seals to create a middle compartment wherein a sparger is positioned for forming bubbles from the gas supplied to the fluid when present in the bag. The bag is rocked to transfer the fluid between the two larger compartments passing through a middle compartment wherein resides a sparger maximizing the gassing and mixing of the fluids. Alternately, the bag can be squeezed using flaps to cause movement of fluid across the three compartments. The seals are staggered between the rows in such a manner as to force fluid to take a deviated path to further improve mixing. The seals can be round or linear or both.

BRIEF DESCRIPTION OF THE DRAWINGS

FIG. 1 is a side view of the apparatus. FIG. 1A is the starting position, FIG. 1B is the bioreactor rocked to the left and FIG. 1C is the bioreactor rocked to the right.

DETAILED DESCRIPTION OF THE INVENTION

Figure 2A:
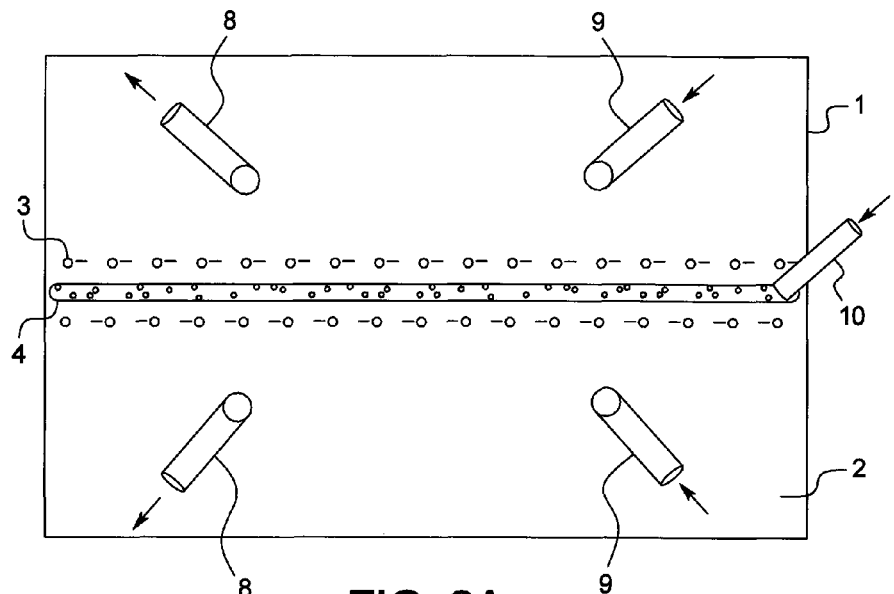
FIG. 2 is a top view of the apparatus.

Reference is now made to FIG. 1, which discloses one embodiment of the apparatus of the present invention in the form of a bag, which is flexible and of a rectangular shape. The bag may be hermetically sealed and may have one or more openings or fittings 9 for introducing or recovering a fluid 2 or exhausting a gas 8 or introducing gas 10 through a sparger 4. FIG. 1 further shows the bag with two rows of seals 3 to create three compartments, the left compartment 12, the middle compartment 11 and the right compartment 1; the sparger 4 is positioned in the middle compartment 11; the bag is placed on a support surface 5 further containing heating element 6 and a rolling means 7 to rock the support surface 5.

FIG. 1B shows that the bioreactor is rocked to the left and FIG. 1C shows the bioreactor rocked to the right.

The flexible the bag 3 may be made from one or more sheets of thin (e.g., having a thickness of between 0.1 and 0.2 millimeters) polyethylene film secured together to define a compartment for receiving the fluid. Preferably, the film used is clear or translucent, although the use of opaque or colored films is also possible.

Figure 2B:
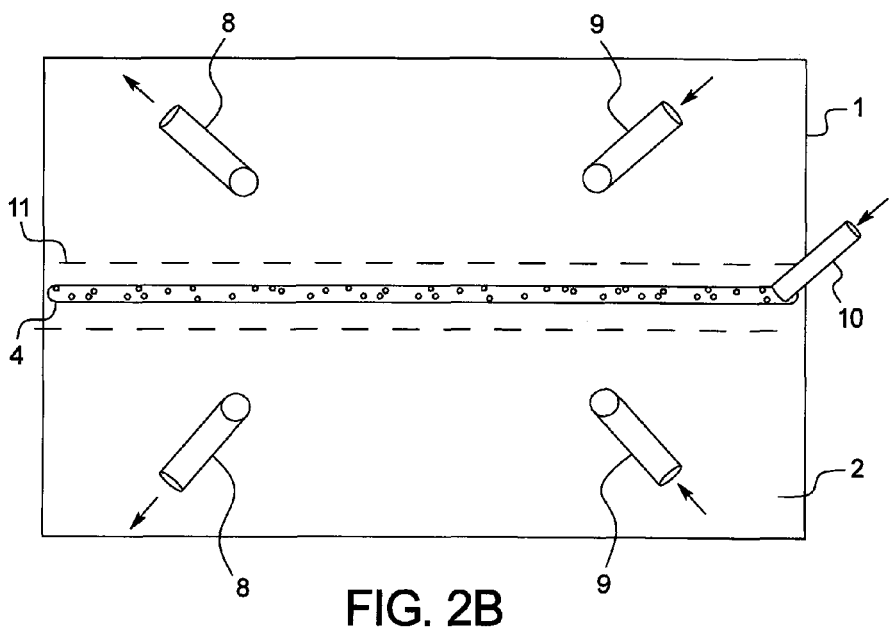

Turning now to FIG. 2, and as noted in the foregoing description, the two rows of proportionally spaced seals create three compartments; by keeping the rows of seals closer to the middle of the bag, a middle compartment is created which is just large enough to contain the sparger. The seal 3 may be in the shape of a dot or a dash and the two rows having staggered positions of seals to force the fluid through a distorted path.

The sparger 4 includes a porous surface attached to the gas inlet 10; the sparging surface can be made from stainless steel, perforated plastic, a membrane or aluminum oxide or any other hard or soft surface capable diffusing gas out as fine bubbles.

It may also be desirable to provide means in the bag to facilitate sensing characteristics of the fluid, such as the pH, oxygen content, temperature, etc. Preferably these sensors are of disposable type and embedded in the bag and remote receivers monitor the response to the sensors.

The preferred embodiment shown in FIG. 1 and FIG. 2 represents a means of mixing the fluid by rocking the bag; alternate means of mixing the fluid will include squeezing the right compartment to force the fluid to pass through the middle compartment and onto the left compartment and vice versa. The bag may be alternately shaken or subject to ultrasonic or mechanical vibrations.

The foregoing descriptions of various embodiments of the present inventions have been presented for purposes of illustration and description. These descriptions are not intended to be exhaustive or to limit the invention to the precise forms disclosed. The embodiments described provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A disposable bioprocessing apparatus intended for receiving a fluid in need of agitation and sparging using a gas, comprising:
   a first sheet of film material having a first peripheral region;
   a second sheet of film material having a second peripheral region and overlapping said first sheet of film material such that said first and second peripheral regions of said first and second sheets of film material are joined together so as to form a peripheral region of a bag and to define an interior space within said bag between said first and second sheets of film material;
   at least two rows of staggered seals sealing said first sheet to said second sheet to create three baffled compartments, right, left and middle, within said bag, the at least two rows of staggered seals including a first row of spaced seals and a second row of spaced seals, the seals in the first row offset from the seals in the second row in a direction substantially perpendicular to a direction of at least one of the first row and the second row;
   at least one sparging rod disposed in said middle compartment and connected to a source of sterile compressed gas;
   a hard surface to support said bag;
   at least one fluid port in said bag;
   at least one gas exhaust port in said bag; and
   at least one gas inlet port in said bag.

2. The apparatus according to claim 1, wherein the hard surface comprises a rocking platform capable of tilting to such an angle as to cause movement of a fluid added to the apparatus from said right compartment to said left compartment passing through said middle compartment and vice versa.

3. The apparatus according to claim 1, further comprising a movable element capable of applying pressure to the apparatus such that a fluid added to the apparatus moves from the left or right compartment to the other compartment passing through said middle compartment and vice versa.

4. The apparatus according to claim 1, wherein said two rows of seals are set 1 to 5 inches apart.

5. The apparatus according to claim 1, wherein said seals are set 0.2 to 2 inches apart.

6. The apparatus according to claim 1, wherein said two rows of seals are generally located in the middle of said bag.

7. The apparatus according to claim 1, wherein said seals are round or linear in shape or a combination of round and linear.

8. The apparatus according to claim 1, wherein said seals in said two rows are staggered to create an indirect path of fluid moving through said middle compartment.

9. The apparatus according to claim 1, further including a sensor for sensing a condition of said fluid in said bag.

10. The apparatus according to claim 1, further including a means of heating or cooling said fluid in said bag.

* * * * *